US008367645B2

(12) United States Patent
Chen

(10) Patent No.: US 8,367,645 B2
(45) Date of Patent: Feb. 5, 2013

(54) COMPOSITIONS AND METHODS FOR TREATING HYPERPROLIFERATIVE DISEASES

(76) Inventor: Chien-Hung Chen, Forest Hills, NY (US)

( * ) Notice: Subject to any disclaimer, the term of this patent is extended or adjusted under 35 U.S.C. 154(b) by 0 days.

(21) Appl. No.: 12/467,640

(22) Filed: May 18, 2009

(65) Prior Publication Data
US 2009/0286760 A1 Nov. 19, 2009

Related U.S. Application Data

(60) Provisional application No. 61/127,883, filed on May 16, 2008, provisional application No. 61/212,072, filed on Apr. 7, 2009.

(51) Int. Cl.
A01N 43/40 (2006.01)
A01N 43/42 (2006.01)
A01N 41/06 (2006.01)
A01N 29/04 (2006.01)
A61K 31/60 (2006.01)
A61K 31/155 (2006.01)

(52) U.S. Cl. ........ 514/165; 514/321; 514/360; 514/601; 514/632; 514/740; 514/754

(58) Field of Classification Search .......................... None
See application file for complete search history.

(56) References Cited

U.S. PATENT DOCUMENTS

| 5,100,919 | A | 3/1992 | Ulrich |  |
| 5,385,915 | A | 1/1995 | Bauxbaum |  |
| 5,721,345 | A * | 2/1998 | Roberfroid et al. | 536/4.1 |
| 5,840,719 | A | 11/1998 | Rubin |  |
| 6,589,944 | B1 | 7/2003 | Rahbar |  |
| 6,927,223 | B1 * | 8/2005 | Meadows et al. | 514/321 |
| 7,329,638 | B2 * | 2/2008 | Yang et al. | 424/185.1 |
| 2002/0045621 | A1 | 4/2002 | Reiner et al. |  |
| 2002/0173511 | A1 | 11/2002 | Wurtman et al. |  |
| 2004/0053900 | A1 | 3/2004 | Masferrer |  |
| 2004/0132758 | A1 * | 7/2004 | Vaccaro et al. | 514/284 |
| 2004/0167114 | A1 | 8/2004 | Fliss |  |
| 2005/0054731 | A1 | 3/2005 | Folli et al. |  |
| 2005/0080074 | A1 | 4/2005 | Wacker et al. |  |
| 2005/0187267 | A1 | 8/2005 | Hamann et al. |  |
| 2006/0040980 | A1 | 2/2006 | Lind et al. |  |
| 2006/0069161 | A1 | 3/2006 | Lee et al. |  |
| 2006/0134206 | A1 * | 6/2006 | Iyer et al. | 424/468 |
| 2006/0147947 | A1 | 7/2006 | Apfeld et al. |  |
| 2006/0276416 | A1 | 12/2006 | Sinclair et al. |  |
| 2007/0015839 | A1 | 1/2007 | Folli et al. |  |
| 2007/0105790 | A1 * | 5/2007 | Khodadoust et al. | 514/34 |
| 2007/0142291 | A1 | 6/2007 | Lin |  |
| 2007/0149466 | A1 | 6/2007 | Milburn et al. |  |
| 2007/0161543 | A1 | 7/2007 | Yu et al. |  |
| 2007/0191351 | A1 | 8/2007 | Cowen et al. |  |
| 2007/0249583 | A1 | 10/2007 | Stein et al. |  |

FOREIGN PATENT DOCUMENTS

| WO | 0182926 A1 | 11/2001 |
| WO | WO01/82926 | 11/2001 |
| WO | 2005023202 A1 | 3/2005 |
| WO | WO2005/023202 | 3/2005 |
| WO | 2006024491 A1 | 3/2006 |
| WO | 2006/078698 | 7/2006 |
| WO | 2007080124 A1 | 7/2007 |
| WO | WO2006/024491 | 3/2009 |
| WO | WO2007/080124 | 7/2009 |

OTHER PUBLICATIONS

Hu et al., "Inhibition of COX-2 by celecoxib enhances glucocorticoid receptor function", Mol. Psychiatry, May 2005, 10(5): 426-28.*
Harris et al., "Chemoprevention of Breast Cancer in Rats by Celecoxib, a Cyclooxygenase 2 Inhibitor", Cancer Research, 60, 2101-2103, Apr. 15, 2000.*
Dowling et al., "Metformin Inhibits Mammalian Target of Rapamycin-Dependent Translation Initiation in Breast Cancer Cells", Cancer Res, 67: 10804-10812, Nov. 15, 2007.*
Sudlow et al. "Cyclic AMP Levels, Adenylyl Cyclase Activity, and Their Stimulation by Serotonin Quantified in Intact Neurons", J Gen Physiol., 1997, vol. 110(3), pp. 243-255; p. 244, col. 1, last para: 5-HT (serotonin creatinine sulfate complex; Sigma Chemical Co.).
Greco et al. "Leptin regulates Tau phosphorylation and Amyloid through AMPK in Neuronal Cells", Biochem Biophys Res Commun., Feb. 27, 2009; vol. 380(1): 98-104.
International Search Report from International Application No. PCT/US10/27330 mailed May 6, 2010.
Beckman, "Great Balls of Fat", Science, Mar. 3, 2006, vol. 311, pp. 1232-1234.
Buhl, et al., "Long-Term AICAR Administration Reducese Metabolic Distrubances and Lowers Blood Pressure in Rats Displaying Feactures of the Insulin Resistance Syndrome", Diabetes, vol. 51, Jul. 2002, pp. 2199-2206.
Daval et al., "Anti-lipolytic Action of AMP-activated protein Kinase in Rodent Adipocytes", J. of Biological Chem., (2005) vol. 280, No. 28, Issue Jul. 1, pp. 25250-25257.
He et al. "Calyculin and okadaic acid promote perilipin phosphorylation and increase lipolysis in primary rat adipocytes", Biochimia et Biophysia Acta 1761 (2006) pp. 247-255.
Kemp et al., "AMP-activated protein kinase, super metabolic regulator", 2003 Biochemical Society, pp. 162-168. Knowler et al., "Reduction in the Incidence of Type 2, diabetes with Lifestyle Intervention or Metformin", N. Eng. J. of Med. vol. 346, No. 6, Feb. 7, 29002: pp. 393-403.
Merrill et al., "Influence of Malonyl-COA and palmintate concentration on rate of palmintate oxidation in rat muscle", J. App. Physiol. Nov. 1998; 85(5):pp. 1909-1914.
Ruderman et al., Amp Kinase and Malonyl-COA: Targets for Therapy of the Metabolic Syndrome, Nat. Rev. Drug Discovery, vol. 3, Apr. 2004, pp. 340-353.
Saha et al., "Activation of Malonyl-COA Decarboxylase in Rat Skeletal Muscle by Contraction and the AMP-activated Protein Kinase Activator 5-Aminoimidazole-4-carboxamide-1-beta-d-ribofuranoside", J. Bio. Chem., vol. (2000) 275, No. 32, Aug. Issue, pp. 24279-24283.

(Continued)

Primary Examiner — Sreeni Padmanabhan
Assistant Examiner — Svetlana M Ivanova
(74) Attorney, Agent, or Firm — Fish & Richardson P.C.

(57) ABSTRACT

The invention relates to a composition that includes a first agent selected including an agent that possesses anti-inflammatory activity or acetaminophen, phenacetin, tramadol and the like; a second agent selected from the group consisting of an oxidative phosphorylation inhibitor, an ionophore, and an adenosine 5-monophosphate-activated Protein kinase (AMPK) activator; a third agent that possesses or maintains serotonin activity.

7 Claims, No Drawings

OTHER PUBLICATIONS

Zhang et al., "Tumor Necrosis Factor-alpha-Stimulates Lipolysis in Differentiated Human Adipocytes Through Activation of Extracellular Signal-Related Kinase and Elevation of Intracellular cAMP", Diabetes, (2002), vol. 51, pp. 2929-2935.

Zhou et al., "Role of AMP-activated protein kinase in mechanism of metformin action", J. of Clin. Investigation, (2001), vol. 108, No. 8, pp. 1167-1174.

International Search Report and Written Opinion issued in corresponding international application PCT/US09/44362, Jun. 19, 2009.

Beckman, "*Great Balls of Fat*", Science, Mar. 3, 2006, vol. 311.

Buhl, et al. "*Long-Term AICAR Administration Reduces Metabolic Disturbances and Lowers Blood Pressure in Rats Displaying Features of the Insulin Resistance Syndrome*", Diabetes, vol. 51, Jul. 2002.

Daval, et al., "*Anti-lipolytic Action of AMP-activated protein Kinase in Rodent Adipocytes*", The Journal of Biological Chemistry, vol. 280, No. 28, Issue of Jul. 1, pp. 25250-25257, 2005.

Fonseca: Clinical cornerstone, 7(2/3):61:72, 2005.

He, et al., "*Calyculin and okadaic acid promote perilipin phosphorylation and increase lipolysis in primary rat adipocytes*", Biochimica et Biophysica Acta 1761 (2006) 247-255.

Kemp, et al. "*AMP-activated protein kinase, super metabolic regulator*", 2003 Biochemical Society, pp. 162-168.

Knowler, et al., "*Reduction in the Incidence of type 2 Diabetes with Lifestyle Intervention or Metformin*", N Engl J. Med. vol. 346, No. 6: Feb. 7, 2002: 393-403.

Merrill, et al., "*Influence of malonyl-CoA and palmitate concentration on rate of palmitate oxidation in rate muscle*", J. App Physiol. Nov. 1998: 85(5) :1909-14.

Muldoon, et al.: J. Clin. Endocrinology & Metabolism, 89(1):266-271, 2004.

Ruderman, et al., "*Amp Kinase and Malonyl-COA: Targets for Therapy of the Metabolic Syndrome*", Nat. Rev. Drug Discovery, vol. 3, Apr. 2004, 340-51.

Saha, et al., "*Activation of Malonyl-CoA Decarboxylase in Rat Skeletal Muscle by Contraction and the AMP-activated Protein Kinase Activator 5-Aminoimidazole-4-carboxamide-1-B-d-ribofuranoside*", J. Bio. Chem., vol. 275, No. 32, Issue of Aug. 11, pp. 24279-24283, 2000.

Zhang, et al., "*Tumor Necrosis Factor-a Stimulates Lipolysis in Differentiated Human Adipocytes Through Activation of Extraceullar Signal-related Kinase and Elevation of Intraceullar cAMP*", Diabetes, vol. 51, Oct. 2002.

Zhou, et al., "*Role of AMP-activated protein kinase in mechanism of metformin action*", The Journal of Clinical Investigation, vol. 108, No. 8, Oct. 2001: 1167-1174.

International Preliminary Report on Patentability issued in international application PCT/US2008/051123.

Extended Search Report issued on Oct. 14, 2009 in European Application No. 09160525.3.

Barnes Christopher J. et al: "Aspirin, but not sodium salicylate, indomethacin, or nabumetone, reversibly suppresses 1,2-dimethylhydrazine-induced colonic aberrant crypt foci in rats", Digestive Diseases and Sciences, vol. 42, No. 5, 1997, pp. 920-926, ISSN: 0163-2116 (abstract only).

Suzuki Kaon et al: "Metformin suppresses the colorectal carcinogenesis via activating AMP protein kinase in the mouse model", Gastroenterology, vol. 134, No. 4, Suppl. 1, Apr. 2008, p. A630 (abstract only).

Yu H -G et al. "The effects of acetylsalicylic acid on proliferation, apoptosis, and invasion of cyclooxygenase-2 negative colon cancer cells", European Journal of Clinical Investigation, vol. 32, No. 11, Nov. 2002, pp. 838-846 (abstract only).

Zakikhani Mahvash et al. "Metformin is an AMP kinase-dependent growth inhibitor for breast cancer cells", Cancer Research, vol. 66, No. 21, (Nov. 1, 2006), pp. 10269-10273.

International Preliminary Report on Patentability issued from International Application No. PCT/US2009/044362 mailed on Nov. 25, 2010.

Zakikhani, M. et al., "Metformin is an AMP Kinase-Dependent Growth Inhibitor for Breast Cancer Cells," Cancer Res. 66: 10269-10273 (2006).

Yu, H.-G., "The Effects of Acetylsalicylic Acid on Proliferation, Apoptosis, and Invasion of Cyclooxygenase-2 Negative Colon Cancer Cells," Eur. J. Clin. Invest., 32: 838-846 (2002).

Barnes, C.J. et al., "Aspirin, But Not Sodium Salicylate, Indomethacin, or Nabumetone, Reversibly Suppresses 1,2-Dimethylhydrazine-Induced Colonic Aberrant Crypt Foci in Rabbits," Digest. Dis. Sci. 42: 920-926 (1997).

\* cited by examiner

COMPOSITIONS AND METHODS FOR TREATING HYPERPROLIFERATIVE DISEASES

CROSS-REFERENCE TO RELATED APPLICATIONS

This application claims benefit to U.S. Provisional Application Ser. No. 61/127,883, filed May 16, 2008, and U.S. Provisional Application Ser. No. 61/212,072, filed Apr. 7, 2009, the contents of which are incorporated herein by reference in their entirety.

BACKGROUND

According to the World Health Organization, there are five million people dying from cancer every year. Drug treatment is one of the three major therapies for cancer. At present, the anticancer directions are as follows: Interfere with or inhibit cell division, Regulate cell generation cycle, Promote tumor cell to apoptosis, Inhibit angiogenesis, Inhibit oncogene, Promote tumor suppressing gene, Tumor antigen, Inhibitor of telomerase and Interfere with information transfer of tumor cells.

In view of the high mortality rates associated with abnormal proliferative diseases including cancer, there exists a need in the art for an effective treatment for benign proliferative diseases as well as cancer.

SUMMARY

This invention is based on the discovery that a combination of certain known drugs is effective in treating hyperproliferative diseases including cancer.

In one aspect, the invention features a composition that includes (A) a first agent that possesses anti-inflammatory activity or acetaminophen, phenacetin, tramadol and the like, a second agent (B) that can be an oxidative phosphorylation inhibitor, an ionophore, or an adenosine 5'-monophosphate-activated Protein kinase (AMPK) activator, and a third agent (C) that possesses or maintains serotonin activity.

The first agent can be any suitable anti-inflammatory compound (e.g., non-steroidal anti-inflammatory compounds) or acetaminophen, phenacetin, tramadol and the like. Examples include aspirin, diclofenac (e.g., diclofenac potassium or diclofenac sodium), ibuprofen (e.g., dexibuprofen or dexibuprofen lysine), indomethacin, nimesulide, and a COX-2 inhibitor (e.g., a nitric oxide-based COX-2 inhibitor or Celebrex® (4-[5-(4-methylphenyl)-3-(trifluoromethyl)-1H-pyrazol-1-yl] benzenesulfonamide)). Other examples of the first agent include Aspirin-arginine, Alxiling, L-arginine acetylsalicylic; Aspirin-DL-lysine; Bismuth Salicylate Basic; Bismuth salicylate; Magnesium Salicylate; Diethylamine Salicylate; Salicylic acid, sodium salt; imidazole salicylate; Sodium Aminosalicylate; Isoniazid Aminosalicylate; Physostigmine Salicylate; Pregnenolone Acetylsalicylate; Choline Magnesium Trisalycylate (Trilisate); Salicylic Acid Zinc Oxide; Sodium Salicylate and Sodium Iodide; Salicylic Acid and Acetic Acid Glacial Solution; and Methyl Salicylate.

The second agent is an oxidative phosphorylation inhibitor, ionophore or AMPK activator). The term "oxidative phosphorylation inhibitor" refers to any suitable agents that inhibit oxidative phosphorylation, such as oxidative phosphorylation uncouplers. An ionophore is a lipid-soluble molecule capable of transporting an ion across the lipid bilayer of cell membranes; and an AMPK activator is an agent that activates AMPK to phosphorylate its substrates, e.g., acetyl-CoA carboxylase and malonyl-CoA decarboxylase. Examples of the second agent include metformin (e.g., metformin chloride), phenformin and buformin.

The third agent can be a compound possessing or maintaining at least one of the serotonin's activities and, when used in combination with the first and second agents, effectively treats one or more of the target diseases of this invention. Examples include serotonin (e.g., serotonin sulfate, serotonin creatinine sulfate complex, or serotonin hydrochloride) and a serotonin re-uptake inhibitor.

A preferred composition of the present invention contains aspirin, metformin hydrochloride, and serotonin creatinine sulfate complex.

In another aspect, the invention features a composition consisting essentially of a first agent that possesses anti-inflammatory activity or acetaminophen, phenacetin, tramadol and the like, a second agent that can be an oxidative phosphorylation inhibitor, an ionophore, or an AMPK activator, and a third agent that possesses serotonin activity. The term "consisting essentially of" used herein limits a composition to the three specified agents and those that do not materially affect its basic and novel characteristics, i.e., the efficacy in treating a target disease described herein. An example of such a composition contains the above-mentioned three agents and a pharmaceutically acceptable carrier. The compositions described above can contain 5-5,000 mg (e.g., 5-3,000 mg, 5-1,500 mg or 5-1,000 mg) of the first agent, 1-5,000 mg (e.g., 1-3000 mg, 1-1,000 mg, 1-500 mg, or 1-100 mg) of the second agent, and 0.1-1,000 mg (e.g., 0.1-100 mg, 0.1-50 mg, or 0.1-30 mg) of the third agent, or in quantities of the same ratio as that calculated based on the above amounts.

In still another aspect, the invention features a method for treating hyperproliferative diseases. The method includes administering to a subject in need thereof an effective amount of one or more of the compositions described above. The diseases mentioned above also include their associated disorders.

The term "treating" or "treatment" used herein refers to administering one or more above-described compositions to a subject, who has a disease described above, a symptom of such a disease, or a predisposition toward such a disease, with the purpose to confer a therapeutic effect, e.g., to cure, relieve, alter, affect, ameliorate, or prevent the disease, the symptom of it, or the predisposition toward it.

The composition described above can be in form suitable for any route of administration. For example, when the composition is orally administered, the present invention in certain embodiments may be administered by any pharmaceutically acceptable oral dosage form including, solids (e.g., tablets, capsules), liquids (e.g., syrups, solutions and suspensions), orally dissolving dosage forms (e.g., orally disintegrating dosage forms, lozenges and troches), powders or granules.

The compositions may also be prepared for parenteral administration as a solution, or suspension. The compositions may also be in dry form ready for reconstitution (e.g., with the additional of sterile water for injection), prior to parenteral administration. Parenteral administration includes administration into any body space or tissue, for example intravenous, intra-arterial, intramuscular and subcutaneous. Where the intended cite of action is a solid tumor, in certain embodiments the composition may be injected directly into the tumor.

In certain other embodiments of the invention, one or more active compounds of the present invention are associated with a carrier substance such as a compound or molecule (e.g., an antibody), to facilitate the transport of the one or more active compounds to the intended cite of action. In certain preferred embodiments, active compound B (useful for treating a hyperproliferating tissue), is covalently bonded to an antibody that corresponds to a marker located on the hyperproliferative tissue. According to this aspect of the invention, it is contemplated that toxicity and adverse effects can be reduced because lower levels of the active agent are capable of providing the desired therapeutic effect relative to administration of the active agent that is not associated with a carrier substance.

The first, second, and third agents described above include active compounds, as well as any pharmaceutically acceptable derivatives such as their salts, pro-drugs, and solvates, if applicable. A salt, for example, can be formed between an anion and a positively charged group (e.g., amino) on an agent. Examples of suitable anions include chloride, bromide, iodide, sulfate, nitrate, phosphate, citrate, methanesulfonate, trifluoroacetate, acetate, chlorophenyoxyacetate, malate, tosylate, tartrate, fumarate, glutamate, glucuronate, lactate, glutarate, benzoate, embonate, glycolate, pamoate, aspartate, parachlorophenoxyisobutyrate, formate, succinate, cyclohexanecarboxylate, hexanoate, octonoate, decanoate, hexadecanoate, octodecanoate, benzenesulphonate, trimethoxybenzoate, paratoluenesulphonate, adamantanecarboxylate, glycoxylate, pyrrolidonecarboxylate, naphthalenesulphonate, 1-glucosephosphate, sulphite, dithionate, and maleate. Likewise, a salt can also be formed between a cation and a negatively charged group (e.g., carboxylate) on an agent. Examples of suitable cations include sodium ion, potassium ion, magnesium ion, calcium ion, and an ammonium cation such as tetramethylammonium ion. In certain embodiments, the agents also include salts containing quaternary nitrogen atoms. Examples of pro-drugs include esters and other pharmaceutically acceptable derivatives, which, upon administration to a subject, are capable of providing active compounds. A solvate refers to a complex formed between an active compound and a pharmaceutically acceptable solvent. Examples of pharmaceutically acceptable solvents include water, ethanol, isopropanol, ethyl acetate, acetic acid, and ethanolamine.

Other examples of the salts include arginine, L-arginine; DL-lysine; Bismuth Salicylate Basic; Bismuth salicylate; Magnesium; Diethylamine; sodium salt; imidazole; Sodium Aminosalicylate; Isoniazid Aminosalicylate; Physostigmine; Pregnenolone Acetylsalicylate; Choline Magnesium Trisalycylate (Trilisate); Zinc Oxide; Iodide; Acetic Acid Glacial Solution and Methyl.

Also within the scope of this invention is one or more compositions described above for use in treating a disease described herein, and the use of such a composition for the manufacture of a medicament for the treatment of a disease described herein.

The details of one or more embodiments of the invention are set forth in the description below. Other features, objects, and advantages of the invention will be apparent from the description and from the claims.

DETAILED DESCRIPTION

In certain embodiments, a composition of this invention can include three agents.

Examples of the first agent can include steroidal anti-inflammatory drugs and non-steroidal anti-inflammatory drugs. Examples of steroidal anti-inflammatory drugs include glucocorticoids, hydrocortisone, cortisone, beclomethasone, dipropionate, betamethasone, dexamethasone, prednisone, methylprednisolone, triamcinolone, fluocinolone acetonide, fludrocortisone, and beclometasone propionate.

Examples of non-steroidal anti-inflammatory drugs (NSAIDs) include A183827, ABT963, aceclofenac, acemetacin, acetyl salicylic acid, AHR10037, alclofenac, alminoprofen, ampiroxicam, amtolmetin guacil, apazone, atliprofen methyl ester, AU8001, benoxaprofen, benzydamine flufenamate, bermoprofen, bezpiperylon, BF388, BF389, BIRL790, BMS347070, bromfenac, bucloxic acid, butibufen, BW755C, C53, C73, C85, carprofen, CBS1108, celecoxib, CHF2003, chlorobiphenyl, choline magnesium trisalicylate, CHX108, cimicoxib, cinnoxicam, clidanac, CLX1205, COX-2 inhibitors, CP331, CS502, CS706, D1367, darbufelone, deracoxib, dexketoprofen, DFP, DFU, diclofenac potassium, diclofenac sodium, diclofenac sodium misoprostol, diflunisal, DP155, DRF4367, E5110, E6087, eltenac, ER34122, esflurbiprofen, etoricoxib, etodolac, F025, felbinac ethyl, fenbufen, fenclofenac, fenclozic acid, fenclozine, fenoprofen, fentiazac, feprazone, filenadol, flobufen, florifenine, flosulide, flubichin methanesulfonate, flufenamic acid, fluprofen, flurbiprofen, FPL62064, FR122047, FR123826, FR140423, FR188582, FS205397, furofenac, GR253035, GW406381, HAI105, HAI106, HCT2035, HCT6015, HGP12, HN3392, HP977, HX0835. HYAL AT2101, ibufenac, ibuproxam-beta-cyclodextrin, icodulinum, IDEA070, iguratimod, imrecoxib, indoprofen, IP751, isoxepac, isoxicam, KC764, ketoprofen, L652343, L745337, L748731, L752860, L761066, L768277, L776967, L783003, L784520, L791456, L804600, L818571, LAS33815, LAS34475, licofelone, LM 4108, lobuprofen, lomoxicam, lumiracoxib, mabuprofen, meclofenamic acid, meclofenamate sodium, mefenamic acid, meloxicam, mercaptoethylguanidine, mesoporphyrin, metoxibutropate, miroprofen, mofebutazone, mofezolac, MX1094, nabumetone, naproxen sodium, naproxen-sodium/metoclopramide, NCX1101, NCX284, NCX285, NCX4016, NCX4215, NCX530, niflumic acid, nimesulide, nitric oxide-based NSAIDs (NitroMed, Lexington, Mass.), nitrofenac, nitroflurbiprofen, nitronaproxen, NS398, ocimum sanctum oil, ONO3144, orpanoxin, oxaprozin, oxindanac, oxpinac, oxycodone/ibuprofen, oxyphenbutazone, P10294, P54, P8892, pamicogrel, parcetasal, parecoxib, PD138387, PD145246, PD164387, pelubiprofen, pemedolac, phenylbutazone, pirazolac, piroxicam, piroxicam beta-cyclodextrin, piroxicam pivalate, pirprofen, pranoprofen, resveratrol, R-ketoprofen, R-ketorolac, rofecoxib, RP66364, RU43526, RU54808, RWJ63556, S19812, S2474, S33516, salicylsalicylic acid, salsalate, satigrel, SC236, SC57666, SC58125, SC58451, SFPP, SKF105809, SKF86002, sodium salicylate, sudoxicam, sulfasalazine, sulindac, suprofen, SVT2016, T3788, TA60, talmetacin, talniflumate, tazofelone, tebufelone, tenidap, tenoxican, tepoxalin, tiaprofenic acid, tilmacoxib, tilnoprofen arbamel, tinoridine, tiopinac, tioxaprofen, tolfenamic acid, tolmetin, triflusal, tropesin, TY10222, TY10246, TY10474, UR8962, ursolic acid, valdecoxib, WAY120739, WY28342, WY41770, ximoprofen, YS134, zaltoprofen, zidometacin, and zomepirac. Other examples of the first agent include acetaminophen, phenacetin, tramadol and the like.

Still other examples of the first agent include Aspirin-arginine, Alxiling, L-arginine acetylsalicylic; Aspirin-DL-lysine; Bismuth Salicylate Basic; Bismuth salicylate; Magnesium Salicylate; Diethylamine Salicylate; Salicylic acid, sodium salt; imidazole salicylate; Sodium Aminosalicylate; Isoniazid Aminosalicylate; Physostigmine Salicylate; Pregnenolone Acetylsalicylate; Choline Magnesium Trisalycylate (Trilisate); Salicylic Acid Zinc Oxide; Sodium Salicylate and Sodium Iodide; Salicylic Acid and Acetic Acid Glacial Solution; and Methyl Salicylate.

Examples of the second agent can include, in addition to those described above, 4,6-dinitro-ocresol, uncoupling proteins (e.g., UCP1, UCP2, or UCP3), carbonyl cyanide p(trifluoromethoxy)phenyl-hydrazone, carbonyl cyanide m-chlorophenyl-hydrazone, C5 gene products, dinitrophenol (e.g., 2,4-dinitrophenol), efrapeptin (A23871), guanethidine, chlorpromazine, amytal, secobarbital, rotenone, progesterone, antimycin A, naphthoquinone, 8-hydroxyquinoline, carbon monoxide, cyanides, azides (e.g., NaN3), dicoumarin, bilirubin, bile pigment, ephedrine, hydrogen sulfide, tetraiodothyronine, quercetin, 2,4-bis(p-chloroanilino)pyrimidine, glyceraldehyde-3 phosphate dehydrogenase, oligomycin, tributyltin chloride, aurovertin, rutamycin, venturicidin, mercurials, dicyclohexylcarbdiimide, Dio-9, m-chlorophenyl-hydrazone mesoxalonitrile, ionomycin, calcium ionophores (e.g., A23187, NMDA, CA 1001, or enniatin B), compounds that increase the Ca+2 concentration in mitochondria (e.g., atractyloside, bongkrekic acid, thapsigargin, amino acid neurotransmitters, glutamate, N-methyl-D-aspartic acid, carbachol, ionophores, inducers of potassium depolarization), apoptogens (i.e., compounds that induce apoptosis), valinomycin, gramicidin, nonactin, nigericin, lasalocid, and monensin. The second agent can be an AMPK activator (e.g., metformin or phenformin, buformin, AICAR, thienopyridones, resveratrol, nootkatone, thiazole, adiponectin, thiazolidinediones, rosiglitazone, pioglitazone or dithiolethiones).

The third agent includes serotonin and its functional equivalents. Examples of the functional equivalents of serotonin include:

Serotonin 1A agonists such as: (e.g., arylpiperazine compounds, azaheterocyclylmethyl derivatives of heterocycle-fused benzodioxans, or buspirone, 3-amino-dihydro-[1]-benzopyrans and benzothiopyrans, (S)-4-[[3-[2-(dimethylamino)ethyl]-1H-indol-5-yl]methyl]-2-oxazolidinone—311C90) and 8-OH-DPAT), 5-Carboxamidotyptamine hemiethanolate maleate salt, N,N-Dipropyl-5-carboxamidotryptamine maleate salt, R(+)-UH-301 HCl, S15535, gepirone, psilocybin, xaliproden HCl and tandospirone;

Serotonin 1B agonists such as: CGS-12066a, N-Methylquipazine dimaleate salt, rizatriptan and naratriptan;

Serotonin 1C agonists such as: dexnorfenfluramine;

Serotonin 1A, 1B, 1D and 1F agonists such as Sumatriptan and 5-Carboxamidotryptamine hemiethanolate maleate salt;

Serotonin 1B and 1D agonists such as: dihydroergotamine and GR46611;

Serotonin 1A and 1D agonists such as: LY-165,163;

Serotonin 1A and 1E agonists such as: ergonovine and BRL 54443 maleate salt;

5-HT 2A/2C agonists such as: DOI (2,5-dimethoxy-4-iodoamphetamine), mCPP (m-chlorophenyl-piperazine), TFMPP (3-Trifluoromethylphenylpiperazine), mescaline, DMT, psilocin, 2C-B, lorcaserin, methylserotonin laleaste salt and 1-(3-Chlorophenyl)piperazine HCl;

Serotonin 2B agonist such as: BW 723C86;

Serotonin receptor 2C modulators such as: (e.g., BVT933, DPCA37215, IK264, PNU22394, WAY161503, R-1065, YM348, VER-3323 hemifumarate and those disclosed in U.S. Pat. No. 3,914,250, WO 01/66548, WO 02/10169, WO 02/36596, WO 02/40456, and WO02/40457, WO 02/44152, WO 02/48124, WO 02/51844, and WO 03/033479), the disclosures of which are incorporated by reference in their entireties;

5-HT 3 agonists such as Phenylbiguanide, O-Methylserotonin HCl, SR 57227A and 1-(3-Chlorophenyl)biguanide HCl;

5-HT 4 agonist such as cisapride, mosapride citrate duhydrate and ML 10302;

5HT7 receptor agonist such as: 4-(2-pyridyl) piperazines, LP 12 hydrochloride hydrate, LP44 and quinoline derivatives;

Serotonin transporter inhibitors such as: imipramine;

Serotonin reuptake inhibitors such as (e.g., arylpyrrolidine compounds, phenylpiperazine compounds, benzylpiperidine compounds, piperidine compounds, tricyclic gamma-carbolines duloxetine compounds, pyrazinoquinoxaline compounds, pyridoindole compounds, piperidyindole compounds, milnacipran, citalopram, sertraline metabolite, demethylsertraline, norfluoxetine, desmethylcitalopram, escitalopram, 1-fenfluramine, femoxetine, ifoxetine, cyanodothiepin, litoxetine, dapoxetine, nefazodone, cericlamine, trazodone, mirtazapine, fluvoxamine, indalpine, indeloxazine, milnacipran, paroxetine, sibutramine, zimeldine, trazodone hydrochloride, dexfenfluramine, bicifadine, vilazodone, desvenlafaxine, duloxetine, amitriptyline, butriptyline, desipramine, dosulepin, doxepin, lofepramine, nortriptyline, protriptyline, trimipramine, amoxapnie, maprotiline, adhyperforin, bromopheniramine, chlorpheniramine, dextromethorphan, diphenhydramine, hyperforin, ketamine, nefazodone, pethidine, phencyclidine, pheniramine, propoxyphene and those in U.S. Pat. No. 6,365,633, WO 01/27060, and WO 01/162341), the disclosures of which are hereby incorporated by reference in their entireties, EPTI, 8-OH-DPAT, Prozac® (fluoxetine hydrochloride) and Zoloft® (Sertraline hydrochloride);

Serotonin and noradrenaline reuptake inhibitors such as: (e.g., venlafaxine, venlafaxine metabolite O-desmethylvenlafaxine, clomipramine, and clomipramine metabolite desmethylclomipramine);

Monoamine re-uptake inhibitors such as: (e.g., amides);

Pyridazinone aldose reductase inhibitors such as: (e.g., pyridazinone compounds);

Serotonergic agents, which are also stimulants of serotonin receptors, such as: (e.g., ergoloid mesylate or pergolide mesylate);

Stimulants of serotonin synthesis such as: (e.g., vitamin B1, vitamin B3, vitamin B6, biotin, Sadenosylmethionine, folic acid, ascorbic acid, magnesium, coenzyme Q10, or piracetam);

Serotonin receptor agonists such as: Rauwolscine, Yohimbine, .alpha.-Methyl-5-hydroxytryptamine, 1-(1-Naphthyl) piperazine, metoclopramide, HTF-919, R-093877, Zolmitriptan, 5-Methoxy-N,N-dimethyltryptamine, 5-MEO-DIPT hydrochloride hydrate and lysergic acid diethylamide;

Serotonin precursors such as tryptophan;

Agents that promote serotonin release from nerve terminals such as: fenfluramine, and norfenfluramine;

All of the compounds mentioned above are known drugs and are readily available to the public. Some of the drugs can be purchased from chemical companies, such as Sigma-Aldrich, St. Louis, Mo. Where the drugs are not readily available, in certain embodiments, one of ordinary skill in art will appreciate that the compounds can be organically manufactured and identified according to accepted standards such as those found in the Merck Index, Remington's Pharmaceutical Sciences, USP/NF, and foreign publications. In certain embodiments, regimens for administering these drug compounds are well known and, if necessary, can be easily re-established by an ordinary skilled clinician. Effective doses will vary, as recognized by those skilled in the art, depending on the type or degree of the disease to be treated; the subject's size, weight, age, and sex; the route of administration; the excipient usage; rate of metabolism, rate of excretion, and the possible co-usage with other therapeutic treatment. In certain embodiments, coadministration of other drugs can lead to increased or decreased metabolism and or excretion requiring an adjustment in dose. In certain other embodiments, where one or more of the active agents are bound to plasma proteins, coadministration of other drugs that effect the extent of binding may also require an adjustment of dose. The daily dose of the compositions described above can be 5-10,000 mg (e.g., 10-5000 or 10-3,000 mg) of the first agent, 1-5,000 mg (e.g., 2-1,000 or 2-3,000 mg) of the second agent, and 0.1-1,000 mg (e.g., 1-50 mg) of the third agent.

In certain preferred embodiments the human dose of the composition of the present invention is about 5-5,000 mg of metformin, about 1-5,000 mg aspirin and about 0.1-1,000 mg serotonin creatinine complex. In certain more preferred embodiments, the human dose of the composition is about 1000 mg of metformin, about 400 mg aspirin and about 4 mg serotonin creatinine complex administered as multiple daily doses. In certain further preferred embodiments, this dose is administered three times a day.

One aspect of this invention features a method of administering an effective amount of one or more of the above-mentioned compositions to a subject for treating a disease described herein. Such a subject can be identified by a health care professional such as a clinician based on results from any suitable diagnostic method. "An effective amount" refers to the amount of one or more compositions described herein that is required to confer a therapeutic effect on a treated subject.

To practice the method of the present invention, in certain embodiments, one or more of the above-described compositions can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion or injection technique.

A sterile injectable composition can be a solution or suspension in a non-toxic parenterally acceptable diluent or solvent, such as a solution in 1,3-butanediol. Examples of the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions.

These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition for topical administration can be prepared in form of an ointment, a gel, a plaster, an emulsion, a lotion, a foam, a cream of a mixed phase or amphiphilic emulsion system (oil/water-water/oil mixed phase), a liposome, a transfersome, a paste, or a powder.

Any of the compositions described above can also be administered in the form of suppositories for rectal administration. It also can be designed such that the composition is released in the intestine. For example, the composition is confined in a solid sub-unit or a capsule compartment that has respectively a matrix or a wall or a closure comprising an enteric polymer which dissolves or disperses at the pH of the small or large intestine to release the drug substance in the intestine. Suitable such polymers have been described above, for example with reference to U.S. Pat. No. 5,705,189.

In certain embodiments, the carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

Benign Tumors

The compounds and methods of the present invention are also suitable for treatment of variety of benign tumors. Exemplary benign tumors include: Adrenal tumors such as adenoma, Adrenal Pheochromocytoma and Adrenal Ganglioneuroma; Brain tumors such as Meningioma and Adenoma; Peripherial Nerve tumors such as Neurofibroma and Schwannoma; Liver tumors such as Adenoma; Thyroid tumors such as Follicular Adenoma; Parathyroid tumors such as Adenoma; Thymus tumors such as Thymoma; Salivary Gland tumors such as Pleomorphic Adenoma; Small Intestine tumor such as Villous Adenoma; Colon tumors such as Tubulovillous Adenoma, Adenomatous Polyp of Colon and Polyposis Coli; Pancreas tumors such as Serous Cystadenoma; Islet tumors such as Pancreatic Islet Cell Tumor; Nasopharyngyl tumors such as Nasal Angiofibroma; Ovary tumors such as: Atypical Proliferating Mucinous Neoplasm, Brenner Tumor of Ovary, Mucinous Cystadenoma, Papillary cystadenoma, Dermoid Cyst of Ovary, Ovarian Teratoma, Ovarian Fibroma, Luteoma and Struma ovarii; Uterus tumors such as Uterine Cellular Leiomyoma and Leiomyoma; Placenta tumors such as Chorioangioma, Partial hydatidiform mole, Complete Hydatidiform and Mole; Bone tumors such as Cavernous Hemangioma and Giant Cell Tumor; Soft Tissue tumors such as Cavernous hemangioma, Desmoid Tumor, lipoma, Myelolipoma and osteochondroma; Joint tumors such as Synovial Chondromatosis; Lung tumors such as Carcinoid Tumor, Granular Cell Tumor and Hemangioma; Myocardium tumors such as Atrial Myxoma; Breast tumors such as Fibroadenoma, Intraductal Papilloma and Schwannoma; Kidney tumors such as Congenital Mesoblastic Nephroma;

and Skin tumors such as Giant Congenital Intradermal Nevus; Kidney tumors such as Congenital Mesoblastic Nephroma.

The present composition can be administered for the treatment of hyperproliferative disorders. The term "hyperproliferative disorders" refers to excess cell proliferation that is not governed by the usual limitation of normal growth. The term denotes malignant as well as nonmalignant cell populations. The excess cell proliferation can be determined by reference to the general population and/or by reference to a particular patient, e.g. at an earlier point in the patient's life. Hyperproliferative cell disorders can occur in different types of animals and in humans, and produce different physical manifestations depending upon the affected cells.

Hyperproliferative cell disorders include tumors as well as nontumors. A "tumor" here refers to an abnormal mass of tissue that results from excessive cell division that is uncontrolled and progressive, also called a neoplasm.

Examples of tumors include a variety of solid tumor such as laryngeal tumors, brain tumors, other tumors of the head and neck; colon, rectal and prostate tumors; breast and thoracic solid tumors; ovarian and uterine tumors; tumors of the esophagus, stomach, pancreas and liver; bladder and gall bladder tumors; skin tumors such as melanomas; and the like, and a fluid tumor such as leukemia.

A "solid tumor", as used herein, refers to an abnormal mass of tissue that usually does not contain cysts or liquid areas. Solid tumors may be benign (not cancerous), or malignant (cancerous). Solid tumors have a distinct structure that mimics that of normal tissues and comprises two distinct but interdependent compartments: the parenchyma (neoplastic cells) and the stroma that the neoplastic cells induce and in which they are dispersed. Different types of solid tumors are named for the type of cells that form them. Examples of solid tumors are sarcomas, carcinomas, and lymphomas.

"Solid tumor" means a locus of tumor cells where the majority of the cells are tumor cells or tumor-associated cells.

More particularly, tumor here refers to either benign (not cancerous) or malignant tumors.
Malignant Tumors Examples of malignant tumors include but not limited to:
Breast cancer:
1. Ductal carcinoma: A1. Ductal Carcinoma In Situ (DCIS): Comedocarcinoma, Cribriform, Papillary, Micropapillary; A2. Infiltrating Ductal Carcinoma (IDC): Tubular Carcinoma, Mucinous (Colloid) Carcinoma, Medullary Carcinoma, Papillary Carcinoma, Metaplastic Carcinoma, Inflammatory Carcinoma
2. Lobular Carcinoma: B1. Lobular Carcinoma In Situ (LCIS); B2. Invasive lobular carcinoma
3. Paget's Disease of the Nipple
Female Reproductive System
CERVIX UTERI: Cervical intraepithelial neoplasia, grade I, Cervical intraepithelial neoplasia, grade II, Cervical intraepithelial neoplasia, grade III (Squamous cell carcinoma in situ), Keratinizing Squamous Cell Carcinoma, Nonkeratinizing Squamous Cell Carcinoma, Verrucous Carcinoma, Adenocarcinoma in situ, Adenocarcinoma in situ, endocervical type, Endometrioid adenocarcinoma, Clear cell adenocarcinoma, Adenosquamous carcinoma, Adenoid cystic carcinoma, Small cell carcinoma, Undifferentiated carcinoma
CORPUS UTERI: Endometrioid carcinoma, Adenocarcinoma, Adenocanthoma (adenocarcinoma with squamous metaplasia), Adenosquamous carcinoma (mixed adenocarcinoma and squamous cell carcinoma, Mucinous adenocarcinoma, Serous adenocarcinoma, Clear cell adenocarcinoma, Squamous cell adenocarcino, Undifferentiated adenocarcinoma OVARY: Serous cystadenoma, Serous cystadenocarcinoma, Mucinous cystadenoma, Mucinous cystadenocarcinoma, Endometrioid tumor, Endometrioid adenocarcinoma, Clear cell tumor, Clear cell cystadenocarcinoma, Unclassified tumor
VAGINA: Squamous cell carcinoma, Adenocarcinoma
VULVA: Vulvar intraepithelial neoplasia, grade I, Vulvar intraipithelial neoplasia, grade II, Vulvar intraepithelial neoplasia, grade III (squamous cell carcinoma in situ), Squamous Cell Carcinoma, Verrucous carcinoma, Padget's disease of the vulva, Adenocarcinoma, NOS, Basal cell carcinoma, NOS, Bartholin's gland carcinoma
Male Reproductive System
PENIS: Squamous Cell Carcinoma
PROSTATE: Adenocarcinoma, Sarcoma, Transitional cell carcinoma of the prostate
TESTIS: Seminomatous tumor, Nonseminomatous tumor, Teratoma, Embryonal carcinoma, Yolk sac tumor, Choriocarcinoma
CARDIAC: sarcoma (angiosarcoma, fibrosarcoma, rhabdomyosarcoma, liposarcoma), myxoma, rhabdomyoma, fibroma, lipoma and teratoma
Respiratory System
LARYNX: Squamous cell carcinoma
PLEURAL MESOTHELIOMA: Primary pleural mesothelioma
PHARYNX: Squamous cell carcinoma
Lung
1. Squamous cell carcinoma (epidermoid carcinoma), Variant: Spindle cell;
2. Small cell carcinoma, Other cell carcinoma, Intermediate cell type, Combined oat cell carcinoma;
3. Adenocarcinoma: Acinar adenocarcinoma, Papillary adenocarcimoma, Bronchiolo-alveolar carcinoma, Solid carcinoma with mucus formation;
4. Large cell carcinoma: Giant cell carcinoma, Clear cell carcinoma, Sarcoma;
Gastrointestinal Tract
AMPULLA OF VATER: Primary adenocarcinoma, Carcinoid tumor, Lymphoma
ANAL CANAL: Adenocarcinoma, Squamous cell carcinoma, Melanoma
EXTRAHEPATIC BILE DUCTS: Carcinoma in situ, Adenocarcinoma, Papillary adenocarcinoma, Adenocarcinoma, intestinal type, Mucinous adenocarcinoma, Clear cell adenocarcinom, Segnet-ring cell carcinoma, Adenosquamous carcinoma, Squamous cell carcinoma, Small cell (oat) carcinoma, Undifferentiated carcinoma, Carcinoma, NOS, Sarcoma, Carcinoid tumor
COLON AND RECTUM: Adenocarcinoma in situ, Adenocarcinoma, Mucinous adenocarcinoma (colloid type; greater than 50% mucinous carcinoma), Signet ring cell carcinoma (greater than 50% signet ring cell), Squamous cell (epidermoid) carcinoma, Adenosquamous carcinoma, Small cell (oat cell) carcinoma, Undifferentiated carcinoma, Carcinoma, NOS, Sarcoma, Lymphoma, Carcinoid tumor
ESOPHAGUS: squamous cell carcinoma, adenocarcinoma, leiomyosarcoma lymphoma
GALLBLADDER: Adenocarcinoma, Adenocarcinoma, intestinal type, Adenosquamous carcinoma, Carcinoma in situ, Carcinoma, NOS, Clear cell adenocarcinoma, Mucinous adenocarcinoma, Papillary adenocarcinoma, Signet-ring cell carcinoma, Small cell (oat cell) carcinoma, Squamous cell carcinoma, Undifferentiated carcinoma LIP AND ORAL CAVITY: Squamous cell carcinoma LIVER: hepatoma (hepatocellular carcinoma), cholangiocarcinoma, hepatoblastoma, angiosarcoma, hepatocellular adenoma, hemangioma EXOCRINE PANCREAS: Duct cell carcinoma, Pleomorphic giant cell carcinoma, Giant cell carcinoma, osteoclastoid type, Adenocarcinoma, Adenosquamous carcinoma, Mucinous (colloid) carcinoma, Cystadenocarcinoma, Acinar cell carcinoma, Papillary carcinoma, Small cell (oat cell) carcinoma, Mixed cell typed, Carcinoma, NOS, Undifferentiated carcinoma, Endocrine cell tumors arising in the islets of Langerhans, Carcinoid SALIVARY GLANDS: Acinic (acinar) cell carcinoma, Adenoid cystic carcinoma (cylindroma), Adenocarcinoma, Squamous cell carcinoma, Carcinoma in pleomorphic adenoma (malignant mixed tumor), Mucoepidermoid carcinoma, Well differentiated (low grade), Poorly differentiated (high grade)

STOMACH: Adenocarcinoma, Papillary adenocarcinoma, Tubular adenocarcinoma, Mucinous adenocarcinoma, Signet ring cell carcinoma, Adenosquamous carcinoma, Squamous cell carcinoma, Small cell carcinoma, Undifferentiated carcinoma, Lymphoma, Sarcoma, Carcinoid tumor SMALL INTESTINE: adenocarcinoma, lymphoma, carcinoid tumors, Karposi's sarcoma, leiomyoma, hemangioma, lipoma, neurofibroma, fibroma Urinary System KIDNEY: Renal cell carcinoma, Carcinoma of Bellini's collecting ducts, Adenocarcinoma, Papillary, Tubular carcinoma, Granular cell carcinoma, Clear cell carcinoma (hypemephroma), Sarcoma of the kidney, Nephroblastoma, Nephroblastoma RENAL PELVIS AND URETER: Transitional cell carcinoma, Papillary transitional cell carcinoma carcinoma, Squamous cell carcinoma, Adenomcarcinoma URETHRA: Transitional cell carcinoma, Squamous cell carcinoma, Adenocarcinoma URINARY BLADDER: Carcinoma in situ, Transitional urothelial cell carcinoma, Papillary transitional cell carcinoma, Squamous cell carcinoma, Adenocarcinoma, Undifferentiated Muscle, Bone, and Soft Tissue BONE: A. Bone-forming: Osteosarcoma; B. Cartilage-forming: Chondrosarcoma, Mesenchymal chondrosarcoma, C. Giant cell tumor, malignant, D. Ewing's sarcoma, E. Vascular tumors: Hemangioendothelioma, Hemangiopericytoma, Angiosarcoma; F. Connective tissue tumors: Fibrosarcoma, Liposarcoma, Malignant mesenchymoma, Undifferentiated sarcoma; G. Other tumors: Chordoma, Adamantinoma of long bones SOFT TISSUES: Alveolar soft-part sarcoma, Angiosarcoma, Epithelioid sarcoma, Extraskeletal chondrosarcoma, Fibrosarcoma, Leiomyosarcoma, Liposarcoma, Malignant fibrous histiocytoma, Malignant hemangiopericytoma, Malignant mesenchymoma, Malignant schwannoma, Rhabdomyosarcoma, Synovial sarcoma, Sarcoma, NOS NERVOUS SYSTEM: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pilealoma), glioblastoma multiform, oligodendroglioma, schwannoma, retinoblastoma, congenital tumors), spinal cord neurofibroma, meningioma, glioma, sarcoma)

HEMATOLOGY: blood (myeloid leukemia (acute and chronic), acute lymphloblastic leukemia, chronic lymphocytic leukemia, myeloproliferative diseases, multiple myeloma, myelodysplastic syndrome), Hodgkin's disease, non-Hodgkin's lymphoma (malignant lymphonoma);

Endocrine System

THYROID GLAND: Papillary carcinoma (including those with follicular foci), Follicular carcinoma, Medullary carcinoma, Undifferentiated (anaplastic) carcinoma NEUROBLASTOMA: Sympathicoblastoma, Sympathicogonioma, Malignant ganglioneuroma, Gangliosympathicoblastma, Ganglioneuroma Skin Squamous cell carcinoma, Spindle cell variant of squamous cell carcinoma, Basal cell carcinoma, Adenocarcinoma developing from sweat or sebaceous gland, Malignant Melanoma Eye THE CONJUNCTIVA: Carcinoma of the conjunctiva;

THE EYELID: Basal cell carcinoma, Squamous cell carcinoma, Sebaceous cell carcinoma;

THE LACRIMAL GLAND: Adenocarcinoma, Adenoid cystic carcinoma, Carcinoma in pleomorphic adenoma, Mucoepidermoid carcinoma, Squamous cell carcinoma;

THE EYELID: Melanoma of the eyelid

THE UVEA: Spindle cell melanoma, Mixed cell melanoma, Epithelioid cell melanoma

SARCOMA OF THE ORBIT: Soft tissue tumor, Sarcoma of bone

RETINOBLASTOMA: Retinoblastoma

Examples of nontumor hyperproliferative disorders include but not limited to myelodysplastic disorders; cervical carcinoma-in-situ; familial intestinal polyposes such as Gardner syndrome; oral leukoplakias; histiocytoses; keloids; hemangiomas; inflammatory arthritis; hyperkeratoses and papulosquamous eruptions including arthritis. Also included are viral induced hyperproliferative diseases such as warts and EBV induced disease (i.e., infectious mononucleosis), scar formation, blood vessel proliferative disorders such as restenosis, atherosclerosis, in-stent stenosis, vascular graft restenosis, etc.; fibrotic disorders; psoriasis; glomerular nephritis; macular degenerative disorders; benign growth disorders such as prostate enlargement and lipomas; autoimmune disorders and the like.

The present composition can also be administered for the treatment of Cardiac dysrhythmias, including but not limited to the Wolff-Parkinson-White syndrome and atrioventricular nodal reentrant tachycardia ventricular tachycardia (VT), atrial tachycardias, atrial flutter and atrial fibrillationsupraventricular tachycardias.

The present composition can also be administered for the treatment of Endometriosis, uterine fibroid (Uterine leiomyomata) menorrhagia, cervical erosion, cervical polyp, and the like.

The present composition can also be administered for the treatment of the defects or disorders of intervertebral discs include but not limited to annular fissures, fragmentation of the nucleus pulposus, and contained herniation a herniated intervertebral disc, degenerative intervertebral discs.

The compositions described above can be preliminarily screened for their efficacy in treating above-described diseases by an in vitro assay and then confirmed by animal experiments (See Examples 1-9 below) and clinic trials. Having the information set forth in the present invention, other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

All of the publications cited herein are incorporated by reference in their entirety.

DETAILED DESCRIPTION OF PREFERRED EMBODIMENTS

Cells can exist in different periods of a cell cycle such as: G1 phase cells, S phase cells, (indicating synthesis and doubling of DNA), and G2 phase cells. Comparing cancer cells to normal cells, one finds a decrease in the proportion of G1 phase cells in cancer, an increase in the proportion of cells in synthesis in cancer and an increase in the proportion of cells in G2 phase and S phase.

Example 1

In Example 1, B20L (Metformin 1 mM+aspirin 0.4 mM+serotonin creatinine sulfate complex 0.002 mM) and B20H (Metformin 10 mM+aspirin 4 mM+serotonin creatinine sulfate complex 0.02 mM) were tested to determine the effect on the cell cycle of pancreatic cancer cells after 24 hours. Each of the cell samples were then tested in a flow cytometer. The testing methodology and equipment used are set forth as follows. Cells were harvested and washed twice with phosphate buffered saline, (PBS) and fixed in 70% cold ethanol at 4° C. overnight. Before analysis, cells were washed twice with PBS, containing 1% bovine serum albumin (BSA), then resuspended with 400 µl PBS and treated with 100 µg/ml RNase A (Roche Diagnostics) and 50 µg/ml propidium iodide (PI) (Sigma). After incubation for 30 min at 37° C., the cells were subjected to DNA content analysis. propidium iodide, (PI) fluorescence was analyzed with a FACS calibur flowcytometer, (Becton Dickinson). Data from at least 10,000 cells were analyzed with software. The results of a control group as well as the two active treatment groups are set forth in Table 1 below.

TABLE 1

Effect of B20L Metformin + aspirin + serotonin creatinine sulfate complex and B20H Metformin + aspirin + serotonin creatinine sulfate complex on Pancreatic Cancer Cells after 24 Hours

| Group | G1 | S | G2 |
|---|---|---|---|
| Control | 63% | 35.5% | 1.5% |
| B20L Metformin 1 mM + aspirin 0.4 mM + serotonin creatinine sulfate complex 0.002 mM | 87.30% | 9.40% | 3.30% |
| Metformin 10 mM + aspirin 4 mM + serotonin creatinine sulfate complex 0.02 mM | 88.70% | 7.80% | 3.40% |

The results indicate that Metformin+aspirin+serotonin creatinine sulfate complex can block pancreatic cancer cells in G1 phase from progressing into S phase and G2 phase after 24 hours as the two treatment groups have a higher proportion of cancer cells in the G1 phase.

Example 2

In Example 2, the testing procedure according to Example 1 above was carried out for 48 and 72 hours comparing the control group to a B20L treatment group. The results are provided in Table 2 below.

TABLE 2

Effect of B20L Metformin + aspirin + serotonin creatinine sulfate complex on Pancreatic Cancer Cells after 48 and 72 Hours

| Group | G1 | S | G2 |
|---|---|---|---|
| The effect of B20L on cell cycle in 48 hours | | | |
| Control | 47% | 46.20% | 6.60% |
| Metformin 1 mM + aspirin 0.4 mM + serotonin creatinine sulfate complex 0.002 mM | 71.70% | 25.40% | 2.90% |
| The effect of B20L on cell cycle in 72 hours | | | |
| Control | 57% | 37.40% | 5.80% |
| Metformin 1 mM + aspirin 0.4 mM + serotonin creatinine sulfate complex 0.002 mM | 63.80% | 31.50% | 4.60% |

The results indicate that Metformin+aspirin+serotonin creatinine sulfate complex can block pancreatic cancer cells in G1 phase from progressing into S phase and G2 phase after 24, 48 and 72 hours as the two treatment groups have a higher proportion of cancer cells in the G1 phase.

Example 3

In Example 3, different dosages of Metformin+aspirin+serotonin creatinine sulfate complex were tested to determine the effect on the cell cycle of breast cancer cells after 24 hours. Each of the cell samples were then tested in a flow cytometer according to the procedures set forth in Example 1 above. The results of a control group as well as the two active treatment groups are set forth in Table 3 below.

TABLE 3

Effect of different dosages of Metformin + aspirin + serotonin creatinine sulfate complex on Breast Cancer Cells after 24 Hours

| Group | G1 | S | G2 |
|---|---|---|---|
| Control | 43% | 46.10% | 10.6% |
| (Metformin 1 mM + aspirin 0.4 mM + serotonin creatinine sulfate complex 0.002 mM) | 59.60% | 36.30% | 4.10% |
| Metformin 10 mM + aspirin 4 mM + serotonin creatinine sulfate complex 0.02 mM | 73.80% | 20.00% | 6.20% |

The results indicate that B20 different dosages of Metformin+aspirin+serotonin creatinine sulfate complex can block breast cancer cells in G1 phase from progressing into S phase cells after 24 hours as the two treatment groups have a lower proportion of cancer S phase cells.

Example 4

In Example 4, different dosages of Metformin+aspirin+serotonin creatinine sulfate complex were tested to determine the effect on proliferation speed of pancreatic cancer cells after 24, 48 and 72 hours. The testing methodology and equipment used are set forth as follows. Pancreatic cancer cells were subcultured into 96-well plates at approximately $4 \times 10^4$ cells per ml and allowed to adhere for 24 h at 37° C. before being treated with the drug. Cell viability was assessed using the Dojindo Cell Counting Kit-8. The cell viability was in direct proportion to the absorbance at 450 nm. Accordingly, the cell viability was expressed as the absorbance at 450 nm. All experiments were performed in triplicate on three separate occasions. The results of a control group as well as the two active treatment groups are set forth in Table 4 below.

TABLE 4

Effect of different dosages of Metformin + aspirin + serotonin creatinine sulfate complex on Proliferation Speed of Pancreatic Cancer Cells after 24, 48 and 72 Hours

| Group | 24 H | 48 H | 72 H |
|---|---|---|---|
| Control | $0.40 \pm 0.023$ | $0.89 \pm 0.053$ | $1.805 \pm 0.033$ |
| Metformin 1 mM + aspirin 0.4 mM + serotonin creatinine sulfate complex 0.002 mM | $0.335 \pm 0.021*$ | $0.725 \pm 0.047**$ | $0.787 \pm 0.066**$ |
| Metformin 10 mM + aspirin 4 mM + serotonin creatinine sulfate complex 0.02 mM | $0.296 \pm 0.017**$ | $0.491 \pm 0.034**$ | $0.565 \pm 0.060**$ |

*$p < 0.05$,
**$p < 0.01$

The results indicate that different dosage of Metformin+aspirin+serotonin creatinine sulfate complex can inhibit pancreatic cancer cell proliferation and the effects are time and dose dependent.

Example 5

In Example 5, Metformin 5 mM; Metformin 5 mM+aspirin 2 mM; and Metformin 5 mM+aspirin 2 mM+serotonin creatinine sulfate complex 0.001 mM were tested to determine the effect on cell cycle on B16 (mice melanoma cells) during the G1, S and G2 cell phases. The procedure for testing using the flow cytometer was carried out as set forth in Example 1 above. The results are set forth in Table 5 below.

TABLE 5

Effect of Metformin 5 mM, Metformin 5 mM + aspirin 2 mM, and Metformin 5 mM + aspirin 2 mM + serotonin creatinine sulfate complex 0.01 mM on B16 mice melanoma cells during G1, S and G2 cell phases.

| Group | G1 | S | G2 |
|---|---|---|---|
| Control | 64 | 12.8 | 23.1 |
| Metformin 5 mM | 71.8 | 4.6 | 23.6 |
| Metformin 5 mM + aspirin 2 mM | 82.4 | 6.0 | 11.6 |
| Metformin 5 mM + aspirin 2 mM + serotonin creatinine sulfate complex 0.01 mM | 85.1 | 6.9 | 8.0 |

The results indicate that metformin was effective. Metformin+aspirin had better effect metformin alone, while metformin+aspirin+serotonin creatinine sulfate complex is better than metformin+aspirin.

Example 6

In Example 6, Metformin 50 mM; Metformin 100 mM, Metformin 150 mM; and metformin 200 mM were tested to determine the kill effect on breast cancer cells after 3, 12 and 24 hours. The testing methodology and equipment used are set forth as follows. Breast cancer cells were subcultured into 96-well plates at approximately $4 \times 10^4$ cells per ml and allowed to adhere for 24 h at 37° C. before being treated with the drug. Cell viability was assessed using the Dojindo Cell Counting Kit-8. The cell viability was in direct proportion to the absorbance at 450 nm. Accordingly, the cell viability was expressed as the absorbance at 450 nm. All experiments were performed in triplicate on three separate occasions. The results are set forth in Table 6 below showing the kill ratio (compared to control group) of different concentrations and different action times of metformin on MCF-7 cells (breast cancer cells).

TABLE 6

Effect of metformin on MCF-7 kill ratio of Breast Cancer Cells after 3, 12 and 24 Hours

| | Time | | |
|---|---|---|---|
| Concentration | 3 h (%) | 12 h (%) | 24 h (%) |
| Metformin 50 mM | $0.139 \pm 0.041**$ | $0.397 \pm 0.042**$ | $0.404 \pm 0.061**$ |
| Metformin 100 mM | $0.123 \pm 0.057**$ | $0.353 \pm 0.083**$ | $0.542 \pm 0.095**$ |
| Metformin 150 mM | $0.318 \pm 0.032**$ | $0.488 \pm 0.036**$ | $0.887 \pm 0.068**$ |
| Metformin 200 mM | $0.321 \pm 0.07**$ | $0.769 \pm 0.088**$ | $0.983 \pm 0.018**$ |

*$p < 0.05$,
**$p < 0.01$

The results indicate that Metformin was effective, can kill breast cancer cell and the effects are time and dose dependent.

Example 7

In Example 7, Metformin+serotonin creatinine sulfate complex+different compounds with anti-inflammatory activity or acetaminophen or tramadol (different first agent), were tested to determine the kill effect on liver cancer cells after 24 and 48 hours. The testing methodology and equipment was carried out as set forth in Example 6 above. The results are set forth in Table 7 below showing the kill ratio (compared to the control group), of different compositions and different action times on HepG-2 cells (liver cancer cells).

TABLE 7

The kill ratio of different compositions and different action times on HepG-2 cells

| | 24 hr (%) | 48 hr (%) |
|---|---|---|
| Metformin 100 mM + aspirin 40 mM + serotonin creatinine sulfate complex 0.2 mM | $0.975 \pm 0.004**$ | $0.995 \pm 0.004**$ |
| Metformin 100 mM + indomethacin 30 mM + serotonin creatinine sulfate complex 0.2 mM | $0.953 \pm 0.010**$ | $0.985 \pm 0.008**$ |

TABLE 7-continued

The kill ratio of different compositions and different action times on HepG-2 cells

| | 24 hr (%) | 48 hr (%) |
|---|---|---|
| Metformin 100 mM + nimesulide 30 mM + serotonin creatinine sulfate complex 0.2 mM | 0.935 ± 0.022** | 0.974 ± 0.007** |
| Metformin 100 mM + celebrex 30 mM + serotonin creatinine sulfate complex 0.2 mM | 0.925 ± 0.027** | 0.971 ± 0.005** |
| Metformin 100 mM + Piroxicam33 mM + serotonin creatinine sulfate complex 0.2 mM | 0.957 ± 0.015** | 0.975 ± 0.009** |
| Metformin 100 mM + diclofenac25 mM + serotonin creatinine sulfate complex 0.2 mM | 0.964 ± 0.016** | 0.981 ± 0.007** |
| Metformin 100 mM + acetaminophen 17 mM + serotonin creatinine sulfate complex 0.2 mM | 0.757 ± 0.115** | 0.969 ± 0.014** |
| Metformin 100 mM + Tramadol hydrochloride 17 mM + serotonin creatinine sulfate complex 0.2 mM | 0.884 ± 0.015** | 0.978 ± 0.008** |

(*p < 0.05, **p < 0.01)

The results indicate that Metformin+serotonin creatinine sulfate complex+different compounds with anti-inflammatory activity, acetaminophen, and tramadol (different first agent), can kill the live cancer cells well, and the effect is better than metformin only.

Example 8

In Example 8, phenformin (different second agent)+serotonin creatinine sulfate complex+different compounds with anti-inflammatory activity or acetaminophen, or tramadol, were tested to determine the kill effect on liver cancer cells after 24 and 48 hours. The testing methodology and equipment was carried out as set forth in Example 6 above. The results are set forth in Table 8 below showing the kill ratio (compared to control group) of different compositions and different action times on HepG-2 cells.

TABLE 8

The kill ratio of different compositions and different actions time on HepG-2 cells

| | 24 hours (%) | 48 hours (%) |
|---|---|---|
| Phenformin 2 mM + aspirin 40 mM + serotonin creatinine sulfate complex 0.2 mM | 0.936 ± 0.016** | 0.991 ± 0.006** |
| Phenformin 2 mM + indomethacin 30 mM + serotonin creatinine sulfate complex 0.2 mM | 0.762 ± 0.032** | 0.920 ± 0.02** |
| Phenformin 2 mM + nimesulide 30 mM + serotonin creatinine sulfate complex 0.2 mM | 0.789 ± 0.039** | 0.956 ± 0.012** |
| Phenformin 2 mM + celebrex 30 mM + serotonin creatinine sulfate complex 0.2 mM | 0.817 ± 0.028** | 0.957 ± 0.002** |
| Phenformin 2 mM + Piroxicam33 mM + serotonin creatinine sulfate complex 0.2 mM | 0.973 ± 0.004** | 0.994 ± 0.007** |
| Phenformin 2 mM + diclofenac25 mM + serotonin creatinine sulfate complex 0.2 mM | 0.965 ± 0.006** | 0.992 ± 0.005** |
| Phenformin 2 mM + acetaminophen 17 mM + serotonin creatinine sulfate complex 0.2 mM | 0.940 ± 0.022** | 0.991 ± 0.005** |
| Phenformin 2 mM + tramadol hydrochloride 17 mM + serotonin creatinine sulfate complex 0.2 mM | 0.721 ± 0.027** | 0.940 ± 0.004** |

(*p < 0.05, **p < 0.01)

The results indicate that phenformin (different second agent)+serotonin creatinine sulfate complex+compounds with different anti-inflammatory activity or acetaminophen, tramadol, can kill the live cancer cell well and the effect is better than metformin only.

Example 9

In Example 9, the effect of B10 (Metformin 50 mg/kg+aspirin 40 mg/kg+serotonin creatinine sulfate complex 0.4 mg/kg) was tested to determine the effect on volume of hepatoma in Strain Kunming Mice (KM) relative to a 10% glucose saline (GS) group. The drugs were administered by intratumor injection, twice a day for 3 days. Volume was measured before and after treatment for each group. The results including the change in volume are set forth in Table 6 below.

TABLE 9

The effect of B10 Metformin 50 mg/kg + aspirin 40 mg/kg + serotonin creatinine sulfate complex 0.4 mg/kg on the volume of hepatoma in KM mice

| Group | Before Drug | After Drug |
|---|---|---|
| 10% G.S. (glucose saline) | 321 ± 54 | 388 ± 275 |
| Metformin 50 mg/kg + aspirin 40 mg/kg + serotonin creatinine sulfate complex 0.4 mg/kg | 219 ± 68 | 13 ± 6** |

(n = 4, *p < 0.05, **p < 0.01)

The results indicate that B10 Metformin 50 mg/kg+aspirin 40 mg/kg+serotonin creatinine sulfate complex 0.4 mg/kg can eliminate hepatoma volume in KM mice at the rate of 94.1%.

Example 10

In Example 10, the effect of B10 Metformin 50 mg/kg+aspirin 40 mg/kg+serotonin creatinine sulfate complex 0.4 mg/kg was tested to determine the effect on the weight and volume of transplanted human hepatoma in hairless mice relative to a 10% GS group and a dehydration alcohol group. The procedures for performing this test were as follows. Hep G2 cells were prepared at $25*10^6$ cells/ml and 0.2 ml of the cell suspension ($5*10^6$ cells) was injected in an exposed mouse mammary fat pad. When tumors achieved the required size (0.5 cm$^3$), animals would be treated with 50 μl of B10, dehydrated alcohol or 10% glucose solution once daily for 6 days. During 12 days after the last injection, tumor volume will be assessed by measuring tumor dimensions (long (L) and short (S)) and estimated it as $V=0.52*L*S^2$. 12 days after the last injection, mice would be sacrificed and tumors would be dissected, weighed and stored in a formaline solution for further evaluation.). Volume was measured before and after treatment for each group. The results including the change in volume are set forth in Table 7 below.

TABLE 10

The effect of B10 on the weight and volume of hepatoma in KM mice

| Group | Volume | | |
|---|---|---|---|
| | Before Treatment | After Treatment | Changes |
| 10% G.S. | 172 ± 65.5 | 444 ± 199 | ↑158% |
| Dehydration ethanol | 188 ± 119 | 89 ± 120** | ↓52.7% |
| Metformin 50 mg/kg + aspirin 40 mg/kg + serotonin creatinine sulfate complex 0.4 mg/kg | 180 ± 128 | 1.05 ± 2.09** | ↓199.4% |

(n = 4, *p < 0.05, **p < 0.01)

The results indicate that B10 can eliminate hepatoma volume in hairless mice at the rate 99.4%, compared to the dehydration ethanol group rate of 52.7%.

Example 11

In Example 11, the effect of B3 (Metformin 50 mg/kg+ celebrex 10 mg/kg+serotonin creatinine sulfate complex 0.4 mg/kg) was tested to determine the effect on metastasis of hepatoma carcinoma H22 cells. Fifty thousand (50,000) mice hepatoma carcinoma H22 cells were injected into the abdominal cavity of KM mice, and then administered 10% G.S. in the control group, or Metformin 50 mg/kg+celebrex 10 mg/kg+serotonin creatinine sulfate complex 0.4 mg/kg two times a day for only the first 30 days in the active treatment group. After treatment was stopped, survival time was observed. The results of the active treatment group and the 10% G.S. group are set forth in Table 8 below.

TABLE 11

Survival Data of KM Mice Treated with Metformin 50 mg/kg + celebrex 10 mg/kg + serotonin creatinine sulfate complex 0.4 mg/kg three times a day for 30 days

| Group | Number Surviving 120 Days | Survival Time |
|---|---|---|
| 10% G.S. | 2/12 | 64.8 ± 27.8 |
| Metformin 50 mg/kg + celebrex 10 mg/kg + serotonin creatinine sulfate complex 0.4 mg/kg | 9/12 | 95 ± 37.9* |

(n = 12, *p < 0.05, **p < 0.01)

The results indicate that the metformin 50 mg/kg+celebrex 10 mg/kg+serotonin creatinine sulfate complex 0.4 mg/kg group, 9 mice survived 120 days, and in the control group only 2 mice survived. The active drug group survival time was also better than control group indicating that this drug therapy can extend mice survival time and reduce cancer cell transplantation rate.

Example 12

In Example 12, the effect of B3 and B10 was tested to determine the effect on oncogenesis rate of hepatoma carcinoma H22 cells in KM mice. Fifty thousand (50,000) mice hepatoma carcinoma H22 cells were injected subcutaneously into KM mice. Treatment groups consisted of B3 and B10, administered three times a day for 30 days. After the drug was stopped, the mice were observed for the presence of tumor tissue to determine whether oncogenesis has occurred. The results of the B10 and B3 treatment groups and the G.S. group are set forth in Table 9 below.

TABLE 12

Oncogenesis Rate for Weeks 1, 2, 3, 4, 6 and 8 After Inoculation and Treatment with B10 (Metformin 50 mg/kg + aspirin 40 mg/kg + serotonin creatinine sulfate complex 0.4 mg/kg) and B3 (Metformin 50 mg/kg + celebrex 10 mg/kg + serotonin creatinine sulfate complex 0.4 mg/kg)

| Group | Time after administration of drug and Oncogenesis Rate | | | | | |
|---|---|---|---|---|---|---|
| | 1 w | 2 w | 3 w | 4 w | 6 w | 8 w |
| GS | 60 | 70 | 70 | 80 | 90 | 90 |
| Metformin 50 mg/kg + aspirin40 mg/kg + serotonin creatinine sulfate complex 0.4 mg/kg | 10 | 20 | 20 | 20 | 20 | 20 |
| Metformin 50 mg/kg + celebrex 10 mg/kg + serotonin creatinine sulfate complex 0.4 mg/kg | 30 | 50 | 50 | 50 | 50 | 50 |

The results indicate that 8 weeks after the drugs were administered, the Metformin 50 mg/kg+aspirin 40 mg/kg+ serotonin creatinine sulfate complex 0.4 mg/kg group only had a 20% oncogenesis rate. The Metformin 50 mg/kg+celebrex 10 mg/kg+serotonin creatinine sulfate complex 0.4 mg/kg only had a 50% oncogenesis rate. Both active drug groups had a lower oncogenesis rate than the control group (90%). Therefore, these drugs can decrease the rate of transplantation of tumor cells.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for treating cancer, consisting essentially of administering to a subject in need thereof an effective amount of a composition consisting essentially of a first agent selected from the group consisting of aspirin and celecoxib; a second agent that is metformin; and a third agent that possesses or maintains serotonin activity that is serotonin creatinine sulfate complex.

2. The method of claim 1, wherein the cancer is a malignant tumor.

3. The method of claim 1, wherein the cancer is a solid tumor.

4. The method of claim 1, wherein the composition consists essentially of 1-5000 mg of the first agent, 5-5000 mg of the second agent, and 0.1-1000 mg of the third agent.

5. The method of claim 1, wherein the composition further consists essentially of a pharmaceutically acceptable carrier.

6. A method for treating cancer, consisting essentially of administering to a subject in need thereof an effective amount of a composition consisting essentially of:
   (a) a first agent that possesses anti-inflammatory activity, wherein the first agent is celecoxib;
   (b) a second agent that is an 5'-monophosphate-activated protein kinase (AMPK) activator, wherein the second agent is metformin; and
   (c) a third agent that possesses or maintains serotonin activity, wherein the third agent is serotonin creatinine sulfate complex.

7. A method for treating cancer, consisting essentially of administering to a subject in need thereof an effective amount of a composition consisting essentially of:
   (a) a first agent that possesses anti-inflammatory activity, wherein the first agent is aspirin;
   (b) a second agent that is an 5'-monophosphate-activated protein kinase (AMPK) activator, wherein the second agent is metformin; and
   (c) a third agent that possesses or maintains serotonin activity, wherein the third agent is serotonin creatinine sulfate complex.

* * * * *

UNITED STATES PATENT AND TRADEMARK OFFICE
CERTIFICATE OF CORRECTION

PATENT NO. : 8,367,645 B2
APPLICATION NO. : 12/467640
DATED : February 5, 2013
INVENTOR(S) : Chien-Hung Chen It is certified that error appears in the above-identified patent and that said Letters Patent is hereby corrected as shown below:

Title Page, Col. 2, item (56) under Other Publications

Line 20, Delete "Reducese" and insert -- Reduces --, therefor.

Line 21, Delete "Distrubances" and insert -- Disturbances --, therefor.

Line 22, Delete "Feactures" and insert -- Features --, therefor.

Line 28-29, Delete "Biochimia et Biophysia Acta" and insert -- Biochimica et Biophysica Acta --, therefor.

Line 31-34, Delete "Knowler et al., "Reducition in the Incidence of Type 2, diabetes with Lifestyle Intervention or Metformin", N. Eng. J. of Med. vol. 346, No. 6, Feb. 7, 29002: pp. 393-403." and insert -- Knowler et al., "Reduction in the Incidence of Type 2, diabetes with Lifestyle Intervention or Metformin", N. Eng. J. of Med. vol. 346, No. 6, Feb. 7, 2002: pp. 393-403. --, on First Page, Col. 2, line 32, as a new Entry.

Line 35, Delete "palmintate" and insert -- palmitate --, therefor.

Line 36, Delete "palmintate" and insert -- palmitate --, therefor.

Signed and Sealed this
Ninth Day of April, 2013

Teresa Stanek Rea
*Acting Director of the United States Patent and Trademark Office*